United States Patent
McClanahan et al.

(10) Patent No.: US 10,314,314 B2
(45) Date of Patent: Jun. 11, 2019

(54) BEDDING INSECTICIDE COMPOSITION

(71) Applicants: Shelia McClanahan, Anderson, IN (US); Gerald Hill, Anderson, IN (US)

(72) Inventors: Shelia McClanahan, Anderson, IN (US); Gerald Hill, Anderson, IN (US)

(*) Notice: Subject to any disclaimer, the term of this patent is extended or adjusted under 35 U.S.C. 154(b) by 0 days.

(21) Appl. No.: 15/928,278

(22) Filed: Mar. 22, 2018

(65) Prior Publication Data
US 2018/0271105 A1    Sep. 27, 2018

Related U.S. Application Data

(60) Provisional application No. 62/474,865, filed on Mar. 22, 2017.

(51) Int. Cl.
| | |
|---|---|
| *A01N 65/22* | (2009.01) |
| *A01N 37/02* | (2006.01) |
| *A01N 65/38* | (2009.01) |
| *A01N 31/02* | (2006.01) |
| *A01N 65/08* | (2009.01) |
| *A01N 25/02* | (2006.01) |
| *A01N 25/06* | (2006.01) |
| *A01N 65/00* | (2009.01) |

(52) U.S. Cl.
CPC ............ *A01N 65/22* (2013.01); *A01N 25/02* (2013.01); *A01N 25/06* (2013.01); *A01N 31/02* (2013.01); *A01N 37/02* (2013.01); *A01N 65/00* (2013.01); *A01N 65/08* (2013.01); *A01N 65/38* (2013.01); *Y02A 50/324* (2018.01); *Y02A 50/344* (2018.01); *Y02A 50/36* (2018.01)

(58) Field of Classification Search
None
See application file for complete search history.

(56) References Cited

U.S. PATENT DOCUMENTS

| | | | |
|---|---|---|---|
| 5,240,708 A | | 8/1993 | Plummer et al. |
| 5,776,478 A | * | 7/1998 | Jain .................. A01N 65/00 424/405 |
| 7,201,926 B2 | * | 4/2007 | Fried ................. A01N 65/00 424/725 |
| 7,211,551 B2 | | 5/2007 | McDonald |
| 9,414,603 B2 | | 8/2016 | Messina |
| 2014/0030203 A1 | | 1/2014 | Dombeck |
| 2015/0216182 A1 | | 8/2015 | Brown et al. |

FOREIGN PATENT DOCUMENTS

CN          101385473 A   *   3/2009

OTHER PUBLICATIONS

Gonzalez-Zamora (Molecules (2013), vol. 18, pp. 13471-13486).*

* cited by examiner

*Primary Examiner* — Susan Hoffman
(74) *Attorney, Agent, or Firm* — Global Intellectual Property Agency, LLC; Daniel Boudwin

(57) ABSTRACT

A bedding insecticide composition for safely exterminating bed bugs is provided. The bedding insecticide composition includes vinegar, liquid dish soap, rubbing alcohol, peppermint extract, rosemary oil, geranium oil, and ground arbol chili seeds. In a preferred embodiment, the bedding insecticide composition is placed within a spray bottle, wherein the composition is applied to a surface containing a bed bug infestation. Once applied, the insecticide composition effectively rids the surface of any bed bugs. The bedding insecticide composition includes environmentally friendly ingredients allowing the composition to be safely used within a home. Alternatively, the bedding insecticide composition may be used on vegetation for exterminating parasitic insects.

2 Claims, No Drawings

BEDDING INSECTICIDE COMPOSITION

CROSS REFERENCE TO RELATED APPLICATION

This application claims the benefit of U.S. Provisional Application No. 62/474,865 filed on Mar. 22, 2017. The above identified patent application is herein incorporated by reference in its entirety to provide continuity of disclosure.

BACKGROUND OF THE INVENTION

The present invention relates to insecticides. More specifically, the present invention provides a bedding insecticide composition for exterminating bed bugs in an environmentally safe manner. The bedding insecticide composition comprises vinegar, liquid dish soap, rubbing alcohol, peppermint extract, rosemary oil, geranium oil, and ground abrol chili seeds.

Infestation of bed bugs within a mattress or bedding is a common problem for many people. Furthermore, many homes are infested with other types of insects throughout the dwelling. To treat these infestations, many people choose to hire exterminators that often use toxic chemicals in order to repel and kill the insects. However, these chemicals are often dangerous to humans and animals within the home. If left untreated, the bed begs may cause harm to the individual sleeping within the bed, while other insects may damage areas within the home. Accordingly, a composition that is configured to kill such insects in a safe manner is desired.

Compositions have been disclosed in the known art that relate to insecticide compositions. These include devices that have been patented and published in patent application publications. These devices generally relate to insecticides for controlling pests, specifically related to insects, spiders, and rodents. These known art compositions have several drawbacks. Many of these compositions fail to provide environmentally friendly ingredients that are safe to use within a home, on bedding, or even on plants. Further, these compositions fail to provide an insecticide composition comprising the combination of vinegar, liquid dish soap, rubbing alcohol, peppermint extract, rosemary oil, geranium oil, and ground abrol chili seeds.

It is submitted that the present invention substantially diverges in design elements from the known art and consequently it is clear that there is a need in the art for an improvement to existing insecticide compositions. In this regard the instant invention substantially fulfills these needs.

SUMMARY OF THE INVENTION

In view of the foregoing disadvantages inherent in the known types of insecticide compositions now present in the known art, the present invention provides a new bedding insecticide composition wherein the same can be utilized for providing convenience for the user when safely exterminating bed bugs that have infested bedding, such as mattresses, sheets, and blankets.

It is therefore an object of the present invention to provide a new and improved bedding insecticide composition that has all of the advantages of the known art and none of the disadvantages.

It is another object of the present invention to provide a bedding insecticide composition comprising vinegar, liquid dish soap, rubbing alcohol, peppermint extract, rosemary oil, geranium oil, and ground arbol chili seeds.

Another object of the present invention is to provide a bedding insecticide composition that is environmentally safe.

Yet another object of the present invention is to provide a bedding insecticide composition that does not stain surfaces.

Another object of the present invention is to provide a bedding insecticide composition that may be readily fabricated from materials that permit relative economy and are commensurate with durability.

Other objects, features and advantages of the present invention will become apparent from the following detailed description.

DETAILED DESCRIPTION OF THE INVENTION

For the purposes of presenting a brief and clear description of the present invention, the preferred embodiment will be discussed as an insecticidal composition used for exterminating bed bugs. The preferred embodiment is for representative purposes only and should not be considered to be limiting in any respect.

The bedding insecticide composition comprises vinegar, liquid dish soap, rubbing alcohol, peppermint extract, rosemary oil, geranium oil, and ground arbol chili seeds. The combination of ingredients are blended together to provide an effective insecticidal spray that specifically targets and kills bed bugs. In the preferred embodiment, the bedding insecticide composition is placed within a spray bottle and adapted to be applied to all bedding materials, such as, pillows, blankets, sheets, mattresses, and pillow cases. The composition is configured to eliminate all bed bugs and bed bug eggs, while further repelling any additional infestation of the sprayed area. The composition is not only safe for use on bedding and other household materials, but it is also not harmful to plants and may be used on infested flora as well.

The bedding insecticide composition comprises 70 to 75% vinegar by weight. The vinegar should comprise about 5% acetic acid ($CH_3COOH$), water, and other trace chemicals. Vinegar is used as a base in the bedding insecticide composition because vinegar is an environmentally friendly solution used for many household cleaning problems. Vinegar is a contact killer, such that when sprayed directly on a bed bug, the bed bug will die. Furthermore, vinegar is used to effectively kill several different species of insects, such as, slugs, moths and ants, thereby allowing the composition to be used on various infestations throughout a home and outdoors.

The bedding insecticide composition further comprises 7 to 12% liquid dish soap by weight. The liquid dish soap can be any brand of household liquid dish soap, such as, Simply Dawn dishwashing detergent. The addition of the liquid dish soap to the composition is adapted to asphyxiate a bed bug when applied thereto. Further, use of the liquid dish soap is environmentally friend and configured to prevent staining of bedding or fabric wherein the composition is applied.

The bedding insecticide composition further comprises 10 to 15% rubbing alcohol by weight. The rubbing alcohol, preferably 92% isopropyl alcohol, is a solvent that effectively kill insects. Rubbing alcohol is also a desiccant, or drying agent, so it can destroy bed bug eggs by drying them out. In addition, rubbing alcohol is used to repel bed bugs by discouraging them from crawling or laying eggs on a surface treated with the insecticide composition. Furthermore, rubbing alcohol is environmentally safe to use and carries no residual staining effect once it has dried.

The bedding insecticide composition further comprises 0.1 to 1.5% peppermint extract by weight. Peppermint extract is an essential oil that is a natural deterrent against most insects. The peppermint extract is adapted to effectively repel bed bugs from laying eggs within a bed or bedding. Peppermint extract is environmentally safe and further repels other insect such as, aphids, squash bugs, white flies, ants, beetles, and fleas. Furthermore, the peppermint extract provides a fresh scent to the bedding insecticide composition, thereby providing a comforting odor to the bedding once the composition is applied.

The bedding insecticide composition further comprises 0.1 to 1.5% rosemary oil by weight. Rosemary oil is a natural oil that has been proven to deter bed bugs, aphids, cabbage moth, and several types of mites. Rosemary is also a deterrent for many plant eating insects. The rosemary oil is adapted to coat the bodies of the insects, effectively suffocating them.

The bedding insecticide composition further comprises 0.1 to 1.5% geranium oil by weight. Geranium oil is an extremely potent repellent for ticks. Addition of the germanium oil to the composition is adapted to repel ticks when the composition is used outdoors, such as, on tall grass areas or bushes.

The bedding insecticide composition further comprises 0.5 to 3% of ground abrol chili seeds by weight. Ground abrol chili seeds are used as a natural insect repellent that is adapted to repel a variety of different insects and pests in addition to bed bugs. The ground chili seeds are adapted to irritate the body of a bed bug, thereby repelling the bed bug from further infesting the bedding or mattress.

In the preferred embodiment of the composition, vinegar is present in 70 to 75% by weight, liquid dish soap is present in 7 to 12% by weight, rubbing alcohol is present in 10 to 15% by weight, peppermint oil extract is present in 0.1 to 1.5% by weight, rosemary oil is present in 0.1 to 1.5% by weight, geranium oil is present in 0.1 to 1.5% by weight, and ground arbol chili seeds are present in 0.5 to 3% by weight.

The preferred embodiment of the bedding insecticide composition is prepared by measuring and weighing the desired ingredients to be used. Next, the ingredients are combined and mixed together until the desired consistency is reached. Once adequately mixed, the composition is placed within a container, such as, a spray bottle or high pressure spraying device. The bedding insecticide composition is then applied to a surface wherein an infestation of bed bugs is located. The amount of the composition applied to the infestation may vary based on size of the infestation. For larger infestations, the composition may be poured directly onto the infested area. Once applied, the insecticide composition is adapted to kill any bed bugs and bed bug eggs, thereby effectively ridding the surface of the insects. Alternatively, the insecticide composition may be used to exterminate common insects within the home. Furthermore, the insecticide composition is safe to use outdoors on a variety of plants.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A bedding insecticide composition, consisting of:
   Vinegar;
   liquid dish soap in an amount sufficient to reduce staining when applied;
   rubbing alcohol in an amount sufficient to hasten drying when applied;
   peppermint extract;
   rosemary oil;
   geranium oil; and
   ground arbol chili seeds.

2. The bedding insecticide composition of claim 1 which consists of by weight:
   70 to 75% vinegar;
   7 to 12% liquid dish soap;
   10 to 15% rubbing alcohol;
   0.1 to 1.5% peppermint extract;
   0.1 to 1.5% rosemary oil;
   0.1 to 1.5% geranium oil; and
   0.5 to 3% of ground arbol chili seeds.

* * * * *